United States Patent [19]

Rooyakkers et al.

[11] Patent Number: 5,275,676
[45] Date of Patent: Jan. 4, 1994

[54] METHOD AND APPARATUS FOR APPLYING A CURVED ELASTIC TO A MOVING WEB

[75] Inventors: Jon P. Rooyakkers; Lyle T. Lamers; David J. Van Eperen, all of Appleton, Wis.

[73] Assignee: Kimberly-Clark Corporation, Neenah, Wis.

[21] Appl. No.: 947,245

[22] Filed: Sep. 18, 1992

[51] Int. Cl.⁵ .................... A41B 13/00; A61F 13/15
[52] U.S. Cl. ..................... 156/164; 156/161; 156/229; 156/494; 156/495; 604/385.2
[58] Field of Search ............... 156/160, 161, 164, 229, 156/494, 495; 604/385.2

[56] References Cited

U.S. PATENT DOCUMENTS

| | | |
|---|---|---|
| 2,884,643 | 5/1959 | Winson . |
| 3,828,367 | 8/1974 | Bourgeois . |
| 3,911,173 | 10/1975 | Sprague, Jr. . |
| 4,031,854 | 6/1977 | Sprague, Jr. . |
| 4,050,462 | 9/1977 | Woon et al. . |
| 4,227,952 | 10/1980 | Sabee . |
| 4,293,367 | 10/1981 | Klasek et al. . |
| 4,417,938 | 11/1983 | Sigl . |
| 4,425,173 | 1/1984 | Frick . |
| 4,464,217 | 8/1984 | Dickover et al. ............. 156/494 X |
| 4,498,944 | 2/1985 | Krause et al. . |
| 4,525,229 | 6/1985 | Suzuki et al. . |
| 4,618,384 | 10/1986 | Sabee . |
| 4,626,305 | 12/1986 | Suzuki et al. . |
| 4,666,542 | 5/1987 | De Jonckheere . |
| 4,711,683 | 12/1987 | Merkatoris . |
| 4,726,873 | 2/1988 | Ales et al. . |
| 4,785,996 | 11/1988 | Ziecker et al. . |
| 4,801,345 | 1/1989 | Dussaud et al. . |
| 4,842,666 | 6/1989 | Werenicz . |
| 4,880,420 | 11/1989 | Pomparelli . |
| 4,915,767 | 4/1990 | Rajala et al. . |
| 4,917,746 | 4/1990 | Kons et al. . |
| 4,992,125 | 2/1991 | Suzuki et al. .................... 156/494 X |
| 4,995,928 | 2/1991 | Sabee . |
| 5,037,415 | 8/1991 | Leroy et al. . |
| 5,236,539 | 8/1993 | Rogberg et al. ................ 156/164 X |

FOREIGN PATENT DOCUMENTS

0475419A1 3/1992 European Pat. Off. .
2234157 1/1991 United Kingdom ................... 2/400

*Primary Examiner*—Jeff H. Aftergut
*Attorney, Agent, or Firm*—Paul Yee

[57] ABSTRACT

A distinctive method and apparatus for applying an elastic member onto a moving substrate along a selected curvilinear location includes a transporting mechanism for moving the substrate along a selected substrate path. A rotatable nip roll contacts the elastic member to place the elastic member onto the substrate along the curvilinear location. A guiding mechanism delivers the elastic member across a free-span distance directly onto the nip roll while selectively changing a lateral positioning of the elastic member relative to a cross direction of the invention. A conveying mechanism directs the elastic member along a selected elastic path into the guiding mechanism, and an elastic supplying mechanism provides the elastic member to the conveying mechanism. In one aspect of the invention, a bonding mechanism provides an adhesive in an arrangement which secures the elastic member to the substrate along the curvilinear location. The adhesive arrangement is configured to substantially avoid contact with the nip roll.

23 Claims, 10 Drawing Sheets

METHOD AND APPARATUS FOR APPLYING A CURVED ELASTIC TO A MOVING WEB

FIELD OF THE INVENTION

The present invention relates to a method and apparatus for applying an elastic member in a curved configuration onto a moving substrate web. More particularly, the present invention relates to a method and apparatus for applying elastic members in a curved configuration at each of the leg opening regions of a disposable absorbent article, such as a disposable diaper.

BACKGROUND OF THE INVENTION

Limited use absorbent articles, such as disposable diapers, have incorporated elasticized gathers at the leg openings of the article. The leg openings are positioned at the lateral side margins of the article, and can be elasticized with a single elastic member or with multiple elastic members. For example, see U.S. Pat. No. 4,050,462 issued Sep. 27, 1977, to Woon et al.

Various techniques have been developed for applying multiple elastic strands onto a substrate. For example, see U.S. Pat. No. 4,666,542 issued May 19, 1987, to DeJonckheere; U.S. Pat. No. 4,626,305 issued Dec. 2, 1986, to Suzuki et al.; and U.S. Pat. No. 4,525,229 issued Jun. 25, 1985, to Suzuki et al.

It has been desirable to employ curved elastic members which better follow the contours of the leg openings formed in the side margins of disposable absorbent garments. For example, techniques for applying an elastic member in a curved pattern, along the lengths of a substrate web have been described in U.S. Pat. No. 4,293,367 issued Oct. 6, 1981, to Klasek et al.; and U.S. Pat. No. 4,915,676 issued Apr. 10, 1990, to Rajala et al.

Conventional techniques, such as those described above, have not provided an adequate system for efficiently placing an elastic member across a desired curvilinear location on the surface of a moving substrate. Typical conventional techniques have incorporated complicated web paths for the elastic members, and have exhibited excessive contact against adhesive coated surfaces of the elastic members. In addition, the conventional techniques have not adequately maintained desired separation spacings between individual elastic strands when the elastic member is composed of multiple strands of elastomeric material.

BRIEF DESCRIPTION OF THE INVENTION

The present invention provides a distinctive apparatus for applying an elastic member onto a substrate along a selected curvilinear location. The apparatus comprises transporting means for moving the substrate along the selected substrate path, and a rotatable nip roll for contacting the elastic member to place the elastic member onto the substrate along the curvilinear location. An elastic supplying means provides the elastic member, and a bonding means provides an adhesive in an arrangement which secures said elastic member to said substrate along said curvilinear location. The adhesive arrangement is configured to substantially avoid contact with said nip roll. A conveying means directs the elastic member along a selected elastic path, and a guiding means is positioned along the elastic path to deliver the elastic member across a free-span distance onto the nip roll while selectively changing a lateral positioning of the elastic member relative to a predetermined cross-direction.

In another aspect of the invention, an apparatus for applying an elastic member onto a substrate along a selected curvilinear location comprises a transporting means for moving the substrate along a selected substrate path, and a rotatable nip roll for contacting the elastic member to place said elastic member onto the substrate along the curvilinear location. A guiding means delivers the elastic member across a free-span distance onto the nip roll while selectively changing a lateral positioning of said elastic member relative to a predetermined cross-direction. The guiding means includes a pivotable arm, and the arm is arranged to pivot about an axis which is aligned generally along the substrate path and generally perpendicular to a selected elastic path into the guiding means. A conveying means directs the elastic member along the selected elastic path into the guiding means, and an elastic supplying means provides the elastic member to the conveying means.

A process aspect of the invention provides a method for applying an elastic member onto a substrate along a selected curvilinear location. The method comprises the step of moving the substrate along a selected substrate path, and contacting the elastic member with a rotatable nip roll which places the elastic member onto the substrate along the curvilinear location. An adhesive is provided in an arrangement which secures said elastic member to said substrate along said curvilinear location and which is configured to substantially avoid contact with said nip roll. The elastic member is guided across a free-span distance onto the nip roll while selectively changing a lateral positioning of the elastic member relative to a predetermined cross-direction. The elastic member is conveyed along a selected elastic path into the guiding step, and the elastic member is supplied into the conveying step.

Another process aspect of the invention provides a method comprising the steps of moving said substrate along a selected substrate path, and contacting said elastic member with a rotatable nip roll which places said elastic member onto said substrate along said curvilinear location. The elastic member is secured to said substrate along the curvilinear location, and the elastic member is delivered across a free-span distance onto said nip roll while a lateral positioning of the elastic member is selectively changed relative to a predetermined cross-direction. The delivering is provided by moving said elastic member with a guide roller mounted on a pivotable arm, and pivoting the arm about an axis which is aligned generally along said substrate path and which is generally perpendicular to a selected elastic path onto the guide roller. The elastic member is conveyed along the selected elastic path into said guiding step, and the elastic member is supplied for movement into the conveying step.

In particular aspects of the invention, the method and apparatus can be configured to apply a plurality of appointed elastic members onto selected side edge portions of the substrate. In other aspects of the invention, the guiding means can comprise a mechanism configured to more effectively place the elastic member across the desired curvilinear location in a periodic arrangement.

The method and apparatus of the present invention can more reliably and efficiently place an elastic member in a selectively curved configuration across the surface of a substrate. The invention can avoid the use of complicated web paths that are more difficult to thread up and more difficult to maintain. Particular aspects of the invention can accommodate a variety of techniques for placing adhesive onto the elastic members, and can reduce undesired contact between construction adhesive and the transport mechanisms of the invention. Where the elastic member is composed of multiple, spaced apart elastic strands, the invention can be configured to more effectively maintain the desired spacings between the individual elastic strands.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various embodiments of the invention will be described in the context of producing a disposable absorbent article, such as a disposable diaper. It is, however, readily apparent that the present invention may also be employed to produce other articles, such as covers, capes, gowns, pants, incontinence garments and the like.

Figure 1:
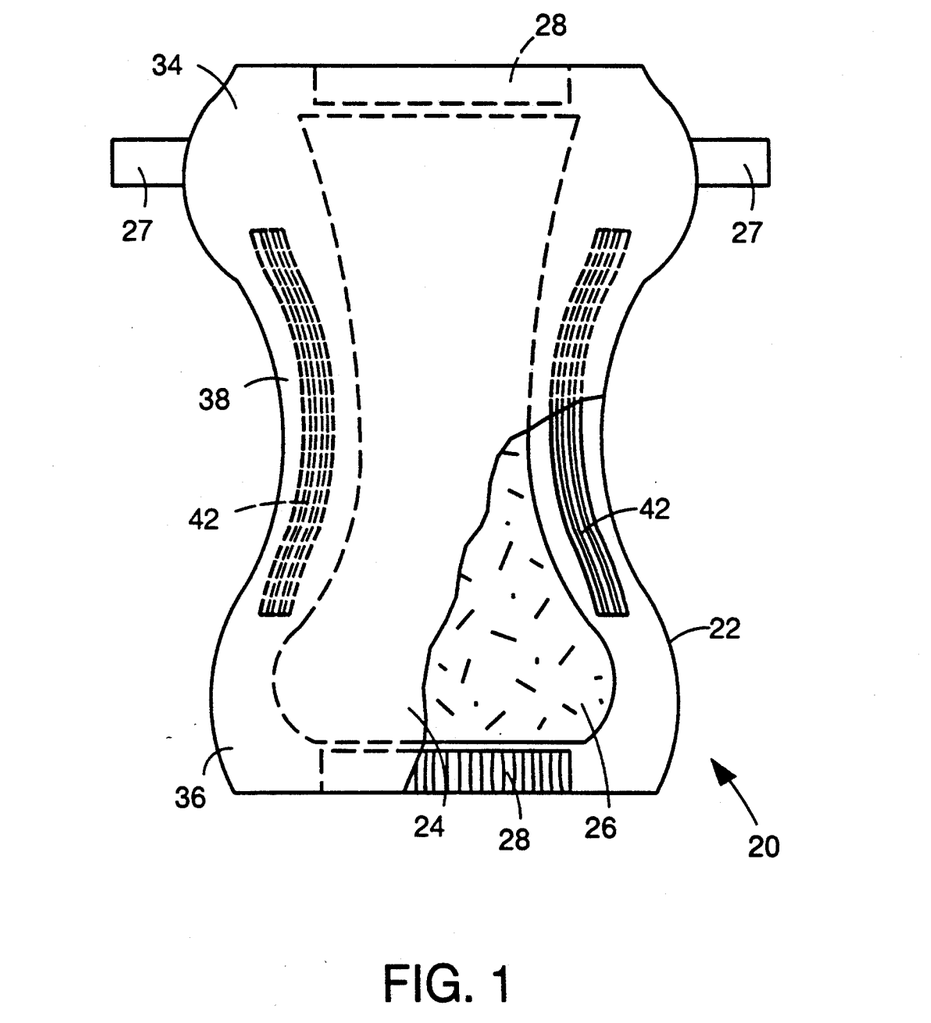
FIG. 1 representatively shows a partially cut away, plan view of a diaper article which incorporates curved leg elastics for elasticizing the leg openings at the side margins of the article.

Disposable articles are typically intended for limited use, and are not intended to be laundered or otherwise cleaned for reuse. For example, a disposable diaper is discarded after it has become soiled by the wearer. With reference to FIG. 1, a representative disposable diaper article is shown in a fully-extended condition with all of its elasticized gathers removed. The garment article represented by disposable diaper 20 has a first waistband section 34, a second waistband section 36, and an intermediate section 38 which interconnects the waistband sections. The diaper comprises a backsheet layer 22, a liquid-permeable topsheet layer 24 superposed in facing relation with the backsheet layer, and an absorbent body 26 interposed between the backsheet and topsheet layers. At least one fastening member 27, and preferably a complementary, opposing pair thereof, is connected to first waistband section 34 of diaper 20. In the illustrated embodiment, fastener 27 is composed of an adhesive tape fastener. Optionally, other types of fasteners, such as Velcro ® type fasteners, snaps, hooks, and the like, may be employed. The fasteners are used to secure the diaper about the waist of the wearer. Further details of a representative diaper are described in U.S. patent application Ser. No. 757,760 entitled "Thin Absorbent Article Having Rapid Uptake of Liquid" filed Sep. 11, 1991 (Attorney Docket No. 9922), the disclosure of which is hereby incorporated by reference to the extent that it is consistent herewith.

Figure 2:
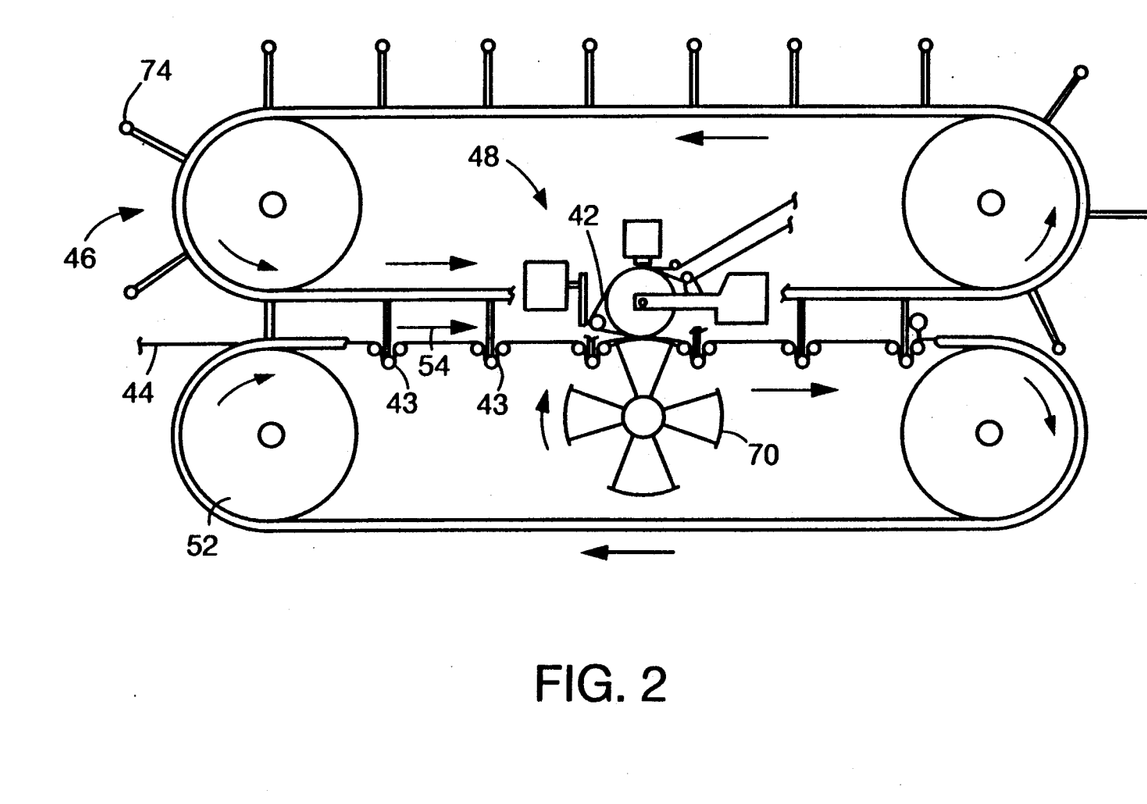
FIG. 2 representatively shows a side elevational view of an apparatus for applying stretched elastic members at selective locations along the surface of a substrate web.
Figure 5:
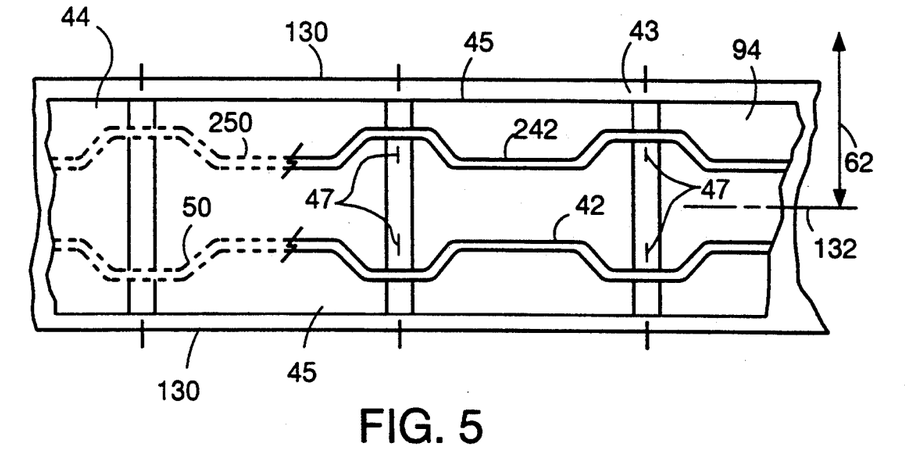
FIG. 5 representatively shows a top plan view of a tucked substrate web onto which periodically curved elastic members have been placed across a pair of selected curvilinear locations.
Figure 5A:
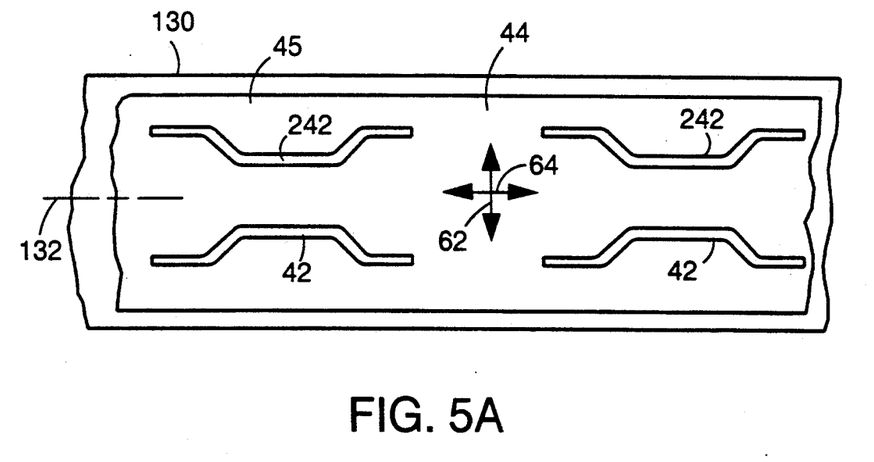
FIG. 5A representatively shows a top plan view of an untucked substrate web onto which separated elastic members have been periodically placed across selected curvilinear locations at spaced apart positions.

FIG. 2 generally shows a suitable mechanism for securing a stretched elastic member 42 onto a moving substrate web 44. For example, the material of substrate 44 may be employed to construct the backsheet component 22 of diaper 20. The stretched elastic applicating unit 46 employs a system of tucker bars 74, which form a regularly spaced series of tuck regions 43 in substrate 44 to provide for an intermittent placement of stretched elastic segments along the length of the substrate. More particularly, the stretched elastic member is secured to the moving substrate web with discrete sections of the stretched elastic bridging across the gaps produced by the plurality of tuck regions 43 (FIG. 5). After the contacting sections of the elastic are attached to the substrate web, the bridging elastic sections are severed with a suitable cutting mechanism along appointed separation lines 47, and the web is then re-extended to operably remove tuck regions 43. Accordingly, the web area incorporated within the previously existing tuck regions will have no portions of elastic member 42 applied thereon. Only the previously untucked sections of web 44 will have sections of elastic member 42 applied and secured thereto. As a result, substrate web 44 will have a selected intermittent placement of stretched, curved elastic segments at spaced apart positions along the length of the substrate (FIG. 5A).

Suitable stretched elastic applicating units are described in U.S. Pat. No. 4,227,952 issued Oct. 14, 1980, to Sabee and U.S. Pat. No. 4,498,944 issued Feb. 12, 1985, to Krause et al., the disclosures of which are hereby incorporated by reference to the extent that they are consistent with the present description.

In the present invention, it is contemplated that elastic member 42 may be either a unitary member composed of elastomeric material, or a composite member having a plurality of individual components. The individual components may all be composed of the same or different elastomeric materials. Alternatively, the composite may include a combination of elastomeric and non-elastomeric components.

Figure 3:
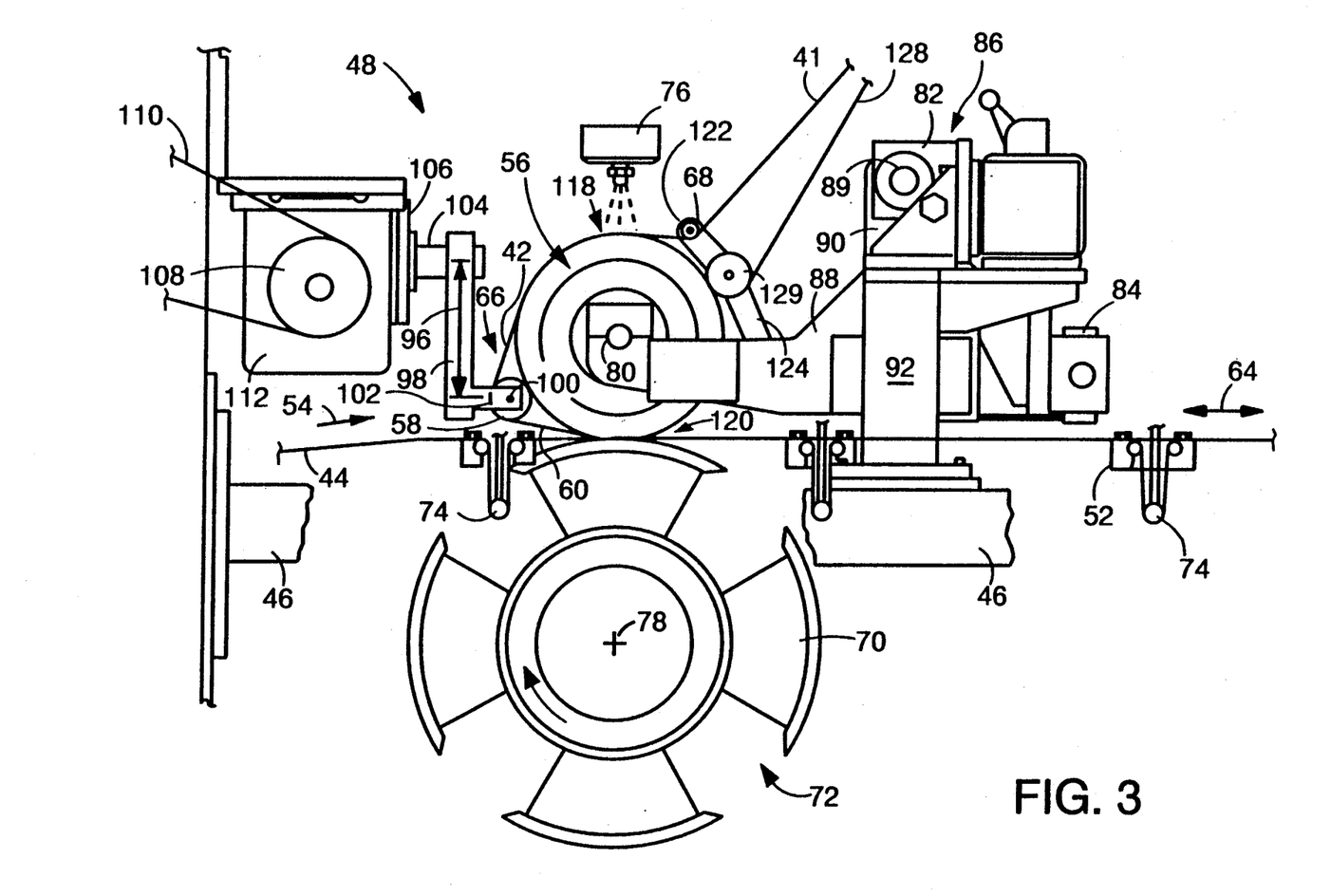
FIG. 3 representatively shows a side elevational view of an apparatus of the invention for applying an elastic member along a curvilinear location extending across the surface of a moving substrate.

To apply a selectively curved elastic member onto to substrate 44, stretched elastic applicating unit 46 can advantageously incorporate a distinctive, curved elastic processing unit 48, such as illustrated in FIG. 3. Processing unit 48 provides an improved apparatus for applying an elastic member 42 onto a moving substrate 44 along a selected curvilinear location 50 (FIG. 5). The apparatus comprises a transporting means, such as a substrate conveyor 52, to move substrate 44 along a selected substrate path 54. A rotatable nip roll 56 contacts elastic member 42 to place the elastic member onto substrate 44 along the appointed curvilinear linear location 50. A guiding means, such as guide roller 58, delivers elastic member 42 across a free-span distance 60 onto an outer peripheral surface of nip roll 56 while selectively changing a lateral positioning of the elastic member relative to a predetermined cross direction 62 (FIG. 5) of the apparatus. Elastic conveying means, such as an upper peripheral surface portion of nip roll 56, directs elastic member 42 along a selected elastic path 66 into the guiding means. Elastic supplying means, such as a mechanism comprising transport roller 68, provides elastic member 42 to the conveying means. A bonding means, such as adhesive applicator 76, provides an adhesive in an arrangement which secures elastic member 42 to substrate 44 along curvilinear location 50. The adhesive arrangement is configured to substantially avoid contact with said nip roll.

For the purposes of the present description, the various aspects of the invention will be described with respect to an individual processing unit 48. It should be understood, however, that particular embodiments of the invention may comprise multiple processing units that are appropriately coordinated with one another to provide desired arrangements of multiple curved elastic members on a selected substrate. Each of the multiple processing units can be configured in accordance with the aspects of the invention described with respect to the individual processing unit 48.

Figures 4, 4A:
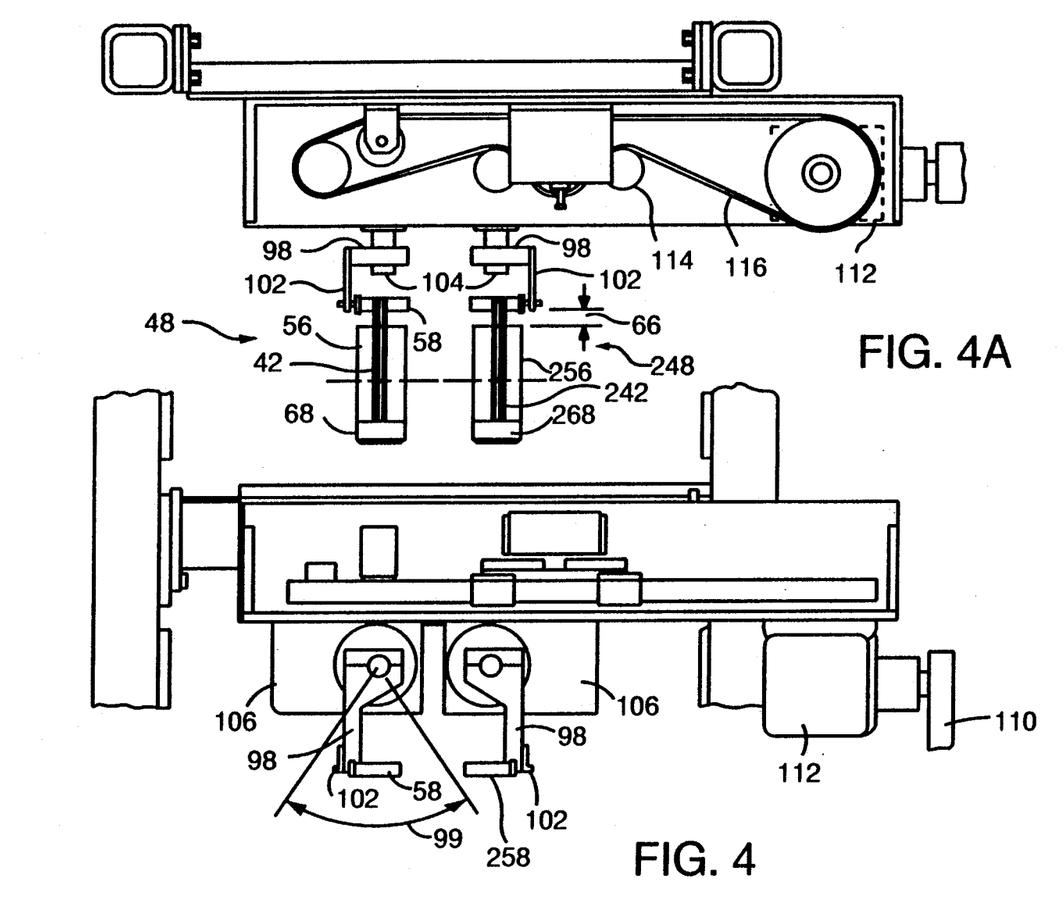
FIG. 4 representatively shows an end elevational view of an apparatus of the invention for applying a complementary pair of curved elastic members.
FIG. 4A representatively shows an top plan view of the apparatus illustrated in FIG. 4.

For example, when constructing a garment article, such as a disposable diaper, it may be desirable to apply a plurality of appointed elastic members onto each of the side edge portions of substrate 44. As illustrated in FIG. 4, the invention can readily be configured to define side edge regions 130 (FIG. 5) which substantially correspond to the side edges 45 of substrate 44. A designated processing unit 48 or 248 can be located in corresponding association with each of the side edge regions 130 to provide a designated curved elastic member secured to substrate 44. Each processing unit includes a designated rotatable nip roll 56 or 256 for contacting an appointed elastic member 42 or 242 to place the appointed elastic member onto substrate 44 along a designated curvilinear location 50 or 250 (FIG. 5). A designated guiding means, such as provided by a mechanism including guide roller 58 or 258, delivers the appointed elastic member across an appointed free-span distance 60 and directly onto the corresponding nip roll 56 or 256. Concurrently, the designated guiding means selectively changes a lateral positioning of the appointed elastic member relative to the cross direction 62 of the apparatus. A designated conveying means, such as provided by a conveying portion 118 of nip roll 56 or a similar conveying portion of nip roll 256, directs the corresponding appointed elastic member along a selected elastic path onto its respective, corresponding guiding means. A designated elastic supplying means, such as one including transport roller 68 or 268, provides the appointed elastic members to their respective conveying means. A designated bonding means, such as adhesive applicator 76, is located in association with each of the side edge regions 130 to provide an adhesive in a designated arrangement which secures the appointed elastic member to substrate 44 along the designated curvilinear location. Each designated adhesive arrangement is configured to substantially avoid contact with its respectively associated nip roll.

As representatively shown in FIG. 5, the curvilinear locations 50 and 250 of the corresponding elastic members 42 and 242 are positioned at each of the two side edges 45 of substrate 44, and can be substantially symmetrically disposed relative to a longitudinal centerline 132 of substrate 44. The configuration of curvilinear location 50 is approximately a mirror image of the oppositely positioned curvilinear location 250.

Referring again to FIG. 3, the illustrated embodiment of the invention has a transporting means for moving substrate 44 which includes a tuck drum 70. The illustrated embodiment of the tuck drum includes a series of recess regions 72 which are substantially equally spaced along the circumferential peripheral surface of the tuck drum. The recess regions are constructed to accommodate the passage of tucker bars 74 employed to form tucks along the length of substrate 44. If the manufacturing process does not employ a tucker bar system, it is readily apparent that the recess regions could then be eliminated, and the peripheral surface of the drum 70 would be substantially continuous.

Tuck drum 70 provides a complementary nipping roll which cooperates with nip roll 56 to form a nip region 120 therebetween. The nip region is employed to position and press elastic member 42 against a major facing surface of substrate 44 for securement along the preselected curved path. In the illustrated embodiment, an adhesive applicator deposits a selected pattern of adhesive, such as a hot melt pressure sensitive adhesive, onto elastic member 42, and the applied adhesive attaches the elastic member onto the surface of substrate 44.

Tuck drum 70 is suitably mounted on a shaft to be rotatable about drum axis 78. The drum is also operatively connected to the machine drive such that the peripheral, surface speed of tuck drum 70 substantially matches the speed at which substrate conveyor 52 is moving substrate 44 along machine direction 64 through the stretched elastic applicating unit 46 (FIG. 2).

The illustrated embodiment of nip roll 56 rides along the peripheral surface of tuck drum 70, and is operably driven by a frictional engagement with respect to the peripheral surfaces of the tuck drum and nip roll. Nip roll 56 has a sufficiently large diameter to permit the nip roll to continuously traverse across recess regions 72 formed along the outer peripheral surface of tuck drum 70. The nip roll is able to bridge across recess regions 72 without disrupting the operation of the stretched elastic applicating unit.

Nip roll 56 is rotatable about nip roll shaft 80, which is aligned along a cross direction 62 of the apparatus. The cross direction is perpendicular to machine direction 64 and generally parallel to substrate 44. Shaft 80 is mounted on a support frame 82 which holds nip roll 56 in operable engagement with tuck drum 70 and substrate 44. The support frame includes support columns 92 and support arm assembly 86, and is constructed and arranged to resiliently urge nip roll 56 against tuck drum 70 with a selected level of engagement or nipping force. In addition, the construction of support frame 82 is able to selectively raise and lower nip roll 56 away and toward tuck drum 70 in a retraction and extension operation to facilitate maintenance.

The shown embodiment of support arm assembly 86 includes a pair of support arms 88 which are positioned side by side in spaced-apart relation. The supporting ends of the support arms are positioned at a distal end of support arm assembly 86 and are configured to operably engage and hold opposite ends of nip roll shaft 80. The support arm assembly is rotatable about a support shaft 89, which is operably held by support cradle 90 to align and position the support shaft generally along cross direction 62 of the apparatus. Support cradle 90 includes a pair of upstanding support columns 92 which are suitably positioned astride substrate 44 and mounted in a substantially fixed position on a suitable support base.

The downward, rotational movement of arm assembly 86 can be selectively controlled with an adjustable mechanical stop, such provided by a moveable jack screw. The mechanical stop can be adjusted to provide for a desired nip between the peripheral surfaces of nip roll 56 and tuck drum 70.

In the illustrated embodiment, the desired levels of contact force between nip roll 56 and tuck drum 70 can, at least in part, be provided by the weight of nip roll 56 and support arms 88. In addition, the level of contact force between nip roll 56 and tuck drum 70 can be provided for by the operation of one or more pneumatic cylinders 84 connected to a first end of support arms 88. The actuation of pneumatic cylinder 84 can, for example, be configured to operably push or pull pivot support arms 88 about support shaft 89 to help decrease or increase the desired contacting force between nip roll 56 and tuck drum 70. The portion of nipping force provided by pneumatic cylinder 84 can also be selectively disengaged, and a retracting mechanism 94 can be connected and operated to selectively rotate support arm assembly 86 about support shaft 89 to raise and lower nip roll 56 relative to tuck drum 70. The retracting operation can, for example, be useful for facilitating machine maintenance.

A retracting mechanism may be mounted on a platform section of support cradle 90 and may employ a remotely positioned lever or cam-type mechanism to perform the desired retraction operation. Alternatively, the retracting mechanism may comprise a pneumatic actuator. For example, the shown embodiment of pneumatic cylinder 84 may be configured to selectively operate in a reverse-mode to push against arm assembly 86 to rotate arms 88 about shaft 89 in a direction which operably raises nip roll 56 up and away from tuck drum 70.

In the embodiment of the invention illustrated by FIG. 3, the guiding means delivers the elastic member across a free-span distance 60 directly onto nip roll 56. During the movement of elastic member 42 from the guiding means to nip roll 56, the elastic member has substantially no engagement with any intermediate components. While delivering the elastic member, the guiding means selectively changes a lateral, cross-directional positioning of elastic member 42. Accordingly, the position of the elastic member extends across a major surface of substrate 44 along a location pathway that curves toward and away from the longitudinal centerline 132 of substrate 44 in a predetermined pattern.

The illustrated embodiment of the guiding means includes a rotatable guide roller 58 carried upon a pivotable arm 98. Guide roller 58 is rotatable about guide roller shaft 100 which is suitably mounted in a support bracket 102. Bracket 102 operably engages the end of guide shaft 100, and also connects to a first, distal end of pivotable arm 98. A second end of pivotable arm 98 is connected to rotatably pivot about pivot shaft 104. The pivot shaft has an axis of rotation which is aligned generally along substrate path 54, which extends generally along machine direction 64. In addition, the pivot axis of shaft 104 is aligned generally perpendicular to the elastic path 66 of elastic member 42 onto guide roller 58. While a perpendicular alignment can provide more optimum performance, it should be understood that some variation from an exact perpendicular can also provide acceptable performance. Such variation is preferably not more than about plus or minus (±) 30 degrees, and more preferably is not more than about ±15 degrees.

Particular aspects of the invention can include controlling means for selectively regulating the guiding means to change the lateral positioning of elastic member 42 in a predetermined pattern. In the illustrated embodiment, the controlling means is configured to continuously adjust the lateral positioning of elastic member 42 in a selected periodic pattern.

In one aspect of the invention, the controlling means can include a cam mechanism for oscillating pivotable arm 98 about pivot shaft 104 through a predetermined periodic cycle pattern. Suitable cam mechanisms are available from CAMCO, a business having offices located at Wheeling, Ill. Vendors, such as CAMCO, are able to design and produce suitable cam mechanisms once they are advised of particular operational parameters. Pertinent parameters can include, for example, the dimensions and inertia of the moving components, the desired number of cycles per minute, and the particular trace pattern desired at the distal, first end of pivotable arm 98.

With reference to FIGS. 4 and 4A, cam box mechanism 106 is operably connected to coordinate with substrate conveyor 52 and the movement of substrate 44 along machine direction 64. In the illustrated embodiment, cam mechanism 106 is operably geared to tuck drum 70 through an appropriate system of properly sized pulleys, such as gear box pulley 108, and belts, such as gear box belt 110, to swing pivotable arm 98 through a desired cycling pattern which oscillates guide roller 58 along cross direction 62 to lay elastic member 42 onto substrate 44 along a desired curvilinear trace which substantially corresponds to the curvilinear location 50 of elastic member 42 across the surface of substrate 44. Gear box pulley 108 connects to a right angle gear box, such as a Model 66, Right Angle Bevel Gear box, available from Hub City Company, a business located in Aberdeen, S. Dak. As representatively shown in FIG. 4A, gear box 112 can be configured to operably drive one or more cam mechanisms 106 through a drive system which includes pulleys 114 and engagement belt 116.

The illustrated embodiment of the invention has a conveying means provided by a peripheral surface portion 118 of nip roll 56. The nip roll conveying portion 118, in the illustrated embodiment, is approximately one upper-quadrant section of the nip roll. Elastic member 42 is directed by conveying portion 118 along a selected elastic path 66 which is approximately perpendicular to both cross-direction 62 and machine-direction 64.

It has been found that the placement location of elastic member 42 onto substrate 44 can more closely match the cross-directional positioning of guide roller 58 when the distance between guide roller shaft 100 and nip region 120 is kept to a minimum. Accordingly, when free-span distance 60 is kept relatively small, the cross-directional positioning of elastic member 42 on substrate 44 can more closely match the cross-directional location and movement of guide roller 58 as it traverses through its pendulum arc carried on pivotable arm 98. If the free-span distance is too short, however, there may be an excessive tendency of elastic member 42 to twist over upon itself. Increasing the free-span distance 60 can reduce the fold-over forces exerted onto elastic member 42. Relatively larger free-span distances 60, however, can also reduce the correspondence between the cross-directional positioning of guide roller 58 and the cross-directional location of elastic member 42 on the substrate.

In particular aspects of the invention, free-span distance 60 is not less than about 4 centimeters. Preferably the free-span distance is not less than about 6 cm, and more preferably is not less than 8 cm. In other aspects of the invention, free-span distance 60 is not more than about 14 cm, preferably is not more than about 12 cm, and more preferably is not more than about 10 cm. Particular aspects of the invention can include a means for adjusting the free-span distance. The shown embodiment, for example, includes a pivotable arm which can be selectively positioned and locked in place at predetermined locations along the length dimension of shaft 104 to thereby adjust the length of free-span distance 60.

In the illustrated embodiment, the effective length 96 of pivotable arm 98 is about 15 centimeters, and the effective length is adjustable to accommodate different desired placements of elastic member 42. The effective length substantially corresponds to the distance of guide roller shaft 100 from the central axis of rotation of pivot shaft 104. It is readily apparent that the length of pivot arm 98 and the angle through which the pivot arm is swung can effectively control the cross-directional distance traversed by guide roller 58 along the cross direction 62 of the apparatus. The longer the length of pivotable arm 98 and/or the greater the angle of oscillation 99 (FIG. 4) imparted to pivotable arm 98, the larger the distance traversed by guide roller 58 during each cycle of cam mechanism 106. Similarly, a smaller length of pivotable arm 98 and/or a smaller angle of oscillation 99 will traverse guide roller 58 through a relatively smaller cross-directional distance during each cycle of the guiding means. In the shown embodiment, the effective length of pivotable arm 98 can be adjusted by moving bracket 102 along the pivotable arm and securing it at the desired length location with a suitable locking mechanism, such as a locking screw clamp.

The angle of oscillation 99 employed in the shown embodiment can be about 23.5 degrees to produce a particular, desired curvilinear location of elastic member 42 onto substrate 44. The resultant location is configured in a periodically undulating pattern wherein the elastic member is positioned along a curved path which varies through a side-to-side, traversing distance of approximately 0.75–1.5 inch measured along cross direction 62.

To afford particular advantages, pivotable arm 98 can be configured to have a rotational oscillation along a plane which is generally aligned with cross direction 62 and generally perpendicular to machine direction 64. With this arrangement, the invention can, for example, generate a smaller change in the length of the path of elastic member 42 between nip region 120 and the point at which the elastic member departs from the conveying portion 118 of the nip roll. In addition, such an arrangement can facilitate the making of very small, incremental adjustments of the distance between roller 58 and nip region 120.

The elastic supplying means for providing elastic member 42 onto the conveying portion of nip roll 56 can include a delivery assembly 122. The shown delivery assembly includes a supporting bracket 124, which connects to support arm assembly 86. Bracket 124 rotatably supports a transport roller 68 which operably directs stretched, elastomeric material 41 onto the conveying portion 118 of nip roll 56. In particular embodiments of the invention, the elastomeric material can comprise a single, substantially unitary ribbon of stretched elastomer. In the illustrated embodiment, the stretched elastic material comprises a plurality of elastic strands, such as three or four individual strands of Lycra ® elastomer. With this embodiment, the outer cylindrical surface of transport roller 68 can include a plurality of spaced-apart grooves each of which is configured to accept therein an individual strand of elastic. The grooves are configured to provide a desired spaced-apart distance between the individual elastic strands. For example, the illustrated embodiment includes four individual elastic strands with adjacent strands spaced apart by a distance of about 0.32 centimeters.

In a particular aspect of the invention, elastic member 42 comprises a composite member composed of multiple, stretched elastic strands secured to a ribbon of carrier sheet material 128. In the illustrated embodiment, for example, carrier sheet 128 may be composed of a polypropylene ribbon having a cross-directional width dimension of about 1.9 centimeters. Carrier sheet 128 is delivered from a suitable supply roll (not shown) employing conventional web supplying techniques well known in the art such as supplying mechanism 129. The carrier sheet can help to maintain desired spaced positionings between individual elastic strands. In addition, the carrier sheet can operably cover any assembly adhesive that has been employed to attach the elastic strands onto substrate 44. Such a configuration can help isolate the adhesive, and help prevent undesired contact between the adhesive and other components of the manufacturing apparatus, such as nip roll 56.

Desired levels of tension and stretch are applied to elastic member 42 prior to delivery onto transport roller 68 and prior to securement onto the carrier sheet. The stretch and tension can be applied using conventional techniques well known in the art. For example, the elastic strands comprising elastic member 42 can be stretched about 200–400 percent employing a conventional system of differential traction rolls operated at different rotational speeds.

Various techniques may be employed to secure elastic member 42 onto substrate 44. For example, a desired attachment may be provided by adhesive bonding, thermal bonding, ultrasonic bonding or the like. In the representatively shown embodiment, elastic member 42 is adhered to substrate 44 with a hot melt, pressure sensitive adhesive, such as a H2096 adhesive available from Findley Adhesives Company, a business having offices at Wauwatosa, Wis. The selected hot melt adhesive is deposited onto elastic member 42 by adhesive applicator 76. The illustrated embodiment of applicator 76 deposits a swirl pattern of overlapping loops of hot melt adhesive onto the elastic member. In particular, the adhesive is applied onto portions of the elastic member that are in contact with or in a close, spaced-adjacent position relative to the conveying portion 118 of nip roll 56. Examples of conventional devices that can be adapted to apply such swirled patterns of hot melt adhesive are described in U.S. Pat. No. 4,031,854 to Sprague Jr. and U.S. Pat. No. 3,911,173 to Sprague Jr. and U.S. Pat. No. 4,785,996 to Ziecker et al. In the illustrated embodiment, adhesive applicator 76 includes adhesive nozzles manufactured by J&M Laboratories, a business having offices at Dawsonville, Ga.

Figure 6:
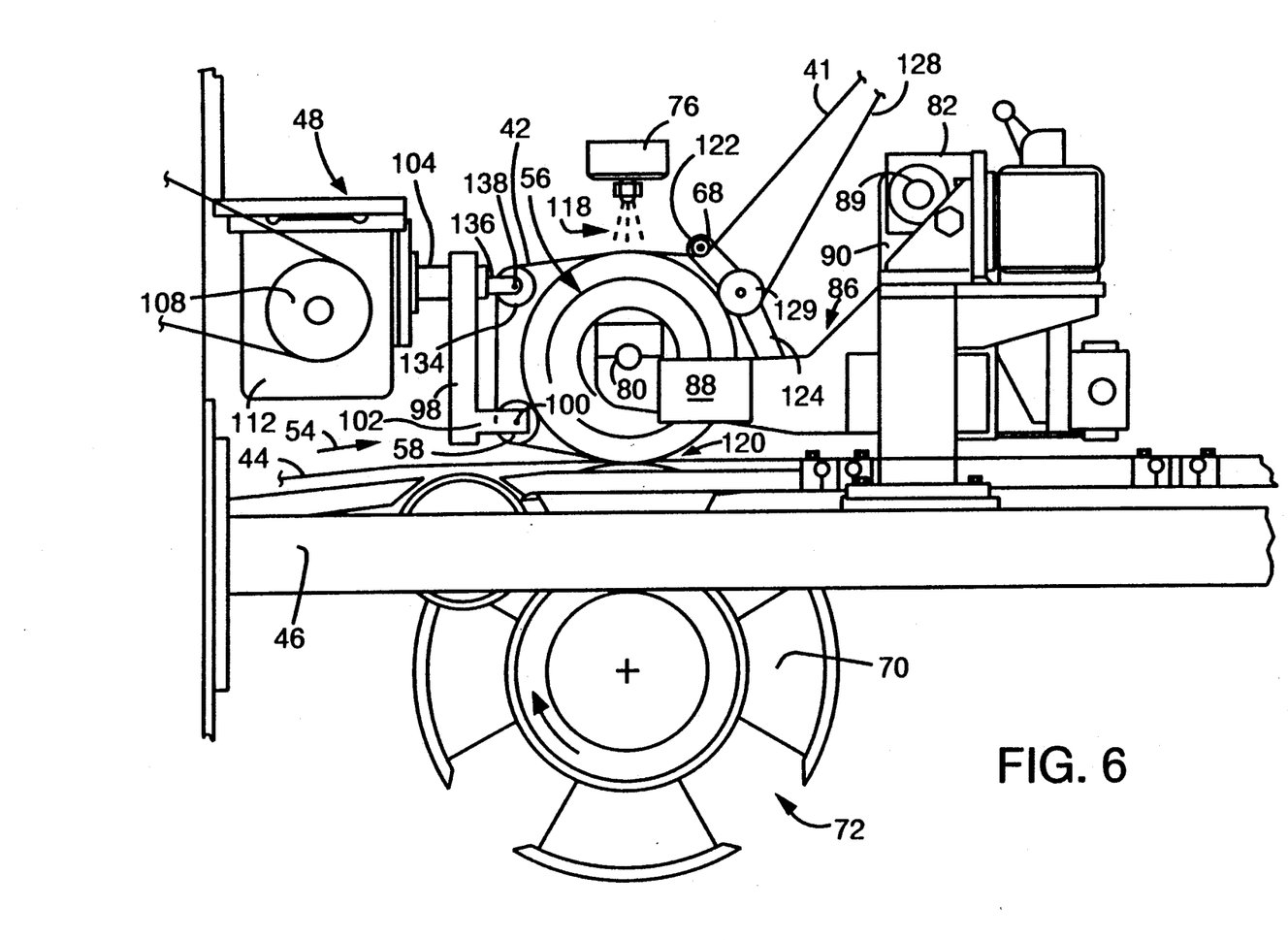
FIG. 6 representatively shows an embodiment of the invention which includes a guiding means having a supplemental guide mechanism.

A particular, alternative aspect of the invention illustrated in FIG. 6 can have a guiding means which includes a supplemental guide mechanism, such as provided by supplemental guide roller 134 and its associated supporting bracket 136. Supplemental guide roller 134 is rotatable about an associated shaft 138, which in the illustrated embodiment is aligned substantially parallel to shaft 100 of the primary guide roller 58. Mounting bracket 136 operably supports and holds shaft 138, and connects to pivotable arm 98. In a particular aspect of the invention, mounting bracket 136 is constructed to selectively position shaft 138 such that the upper, horizontal tangent line to guide roller 134 is in substantial alignment with the longitudinal axis of rotation of pivot shaft 104. As a result, the rotational movement of pivotable arm 98 about pivot shaft 104 can generate a twisting motion to supplemental guide roller 134 which selectively cants the axis of shaft 138 relative to the conveying portion 118 of nip roll 56. Elastic member 42 is threaded over supplemental guide roller 134 and contacts the peripheral surface thereof. When supplemental guide roller 134 twists about the axis of rotation of pivot shaft 104, the contacting surface of supplemental guide roller can impart an oscillating, substantially pure twisting action to elastic member 42. As a result, supplemental roller 134 can more effectively change the direction of movement of elastic member 42 and direct it toward guide roller 58 while generating lower side forces against the elastic member. The reduced levels of side force can advantageously reduce the tendency of the elastic member to fold over upon itself while the oscillating movement of guide roller 58 is operating to change the lateral positioning of the elastic member along the desired curvilinear location which traverses across the surface of substrate 44.

The illustrated embodiment of applicator nip roll 56 is an approximately 20.3 centimeter diameter, cylindrical roll having an axial width of about 8.6 centimeters and having an outer surface composed of silicone rubber. Tuck drum 70 is an approximately 40 centimeter diameter, cylindrical roll having an axial width dimension of about 38 centimeters. Recess regions 72 can, for example, extend radially into the tuck drum for a distance of about 11 centimeters. It is readily apparent that the circumferential length and radial depth of recess regions 72 can be modified to suitably accommodate the placement of tucker bars therein during the operation of the apparatus. Where the apparatus is configured to not include the tucker bar mechanisms, the recess regions may be eliminated from drum 70. Accordingly, the peripheral cylindrical surface of drum 70 would then be substantially continuous. For example, U.S. Pat. No. 4,711,683 issued Dec. 8, 1987 to Merkatoris describes an alternative technique for applying stretched elastics onto a moving substrate without employing a tucker bar system.

Figure 7:
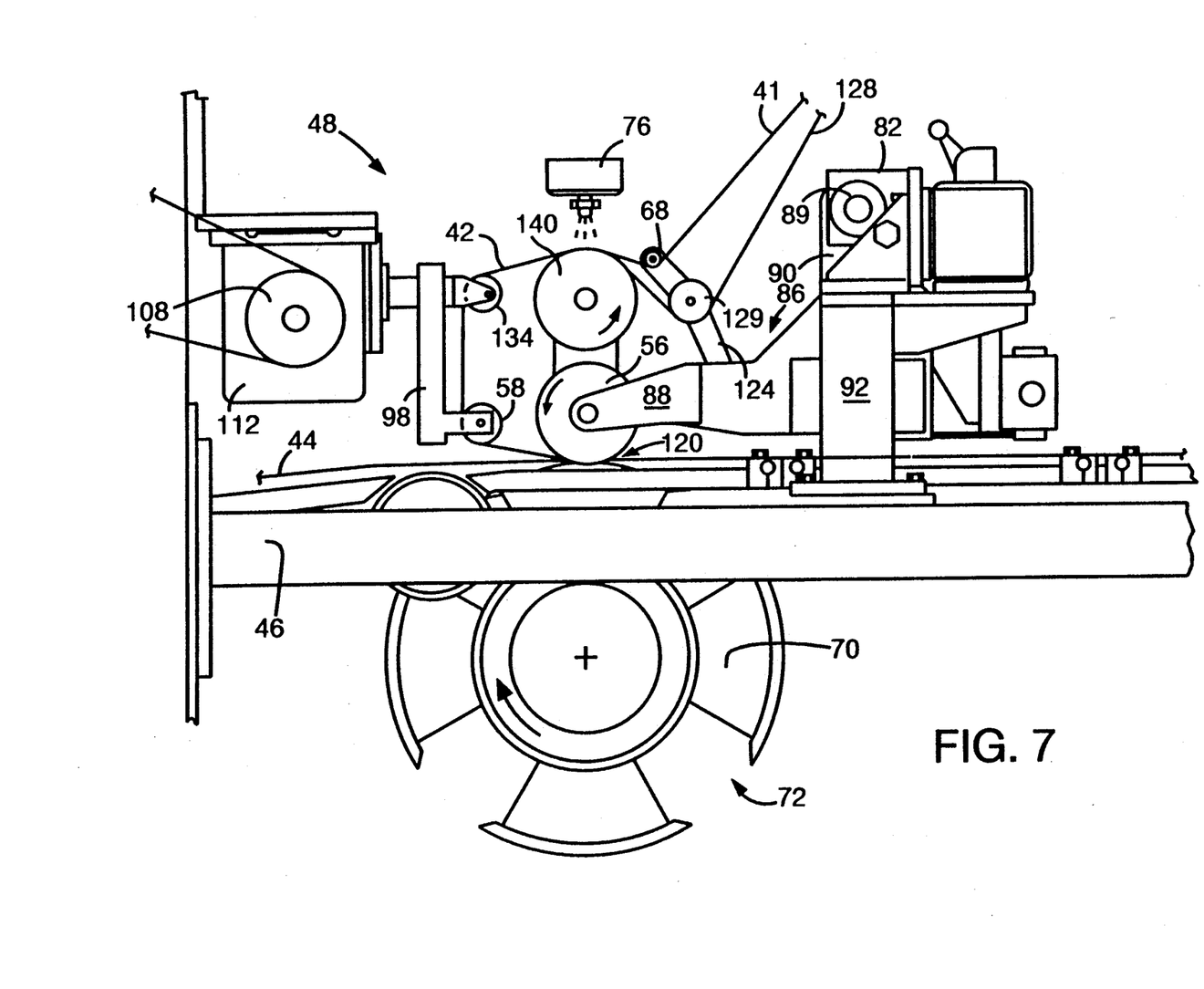
FIG. 7 representatively shows an embodiment of the invention which includes a transporting means having a supplemental transport mechanism.

A further aspect of the invention may include a transporting means which includes a supplemental transport mechanism, such as a separate applicator roll. As representatively shown in FIG. 7, for example, applicator roll 140 provides a transport mechanism which is separate and spaced away from nip roll 56. As a result, the constructions of nip roll 56 and applicator roll 140 can be individually tailored to meet different processing parameters. For example, it may be desireable to selectively heat or chill applicator roll 140 to better accommodate the process of applying adhesive onto elastic member 42. Alternatively, the applicator roll may be separately adapted and configured to provide a complementary component of a sonic bonding or thermal bonding operation.

Figure 8:
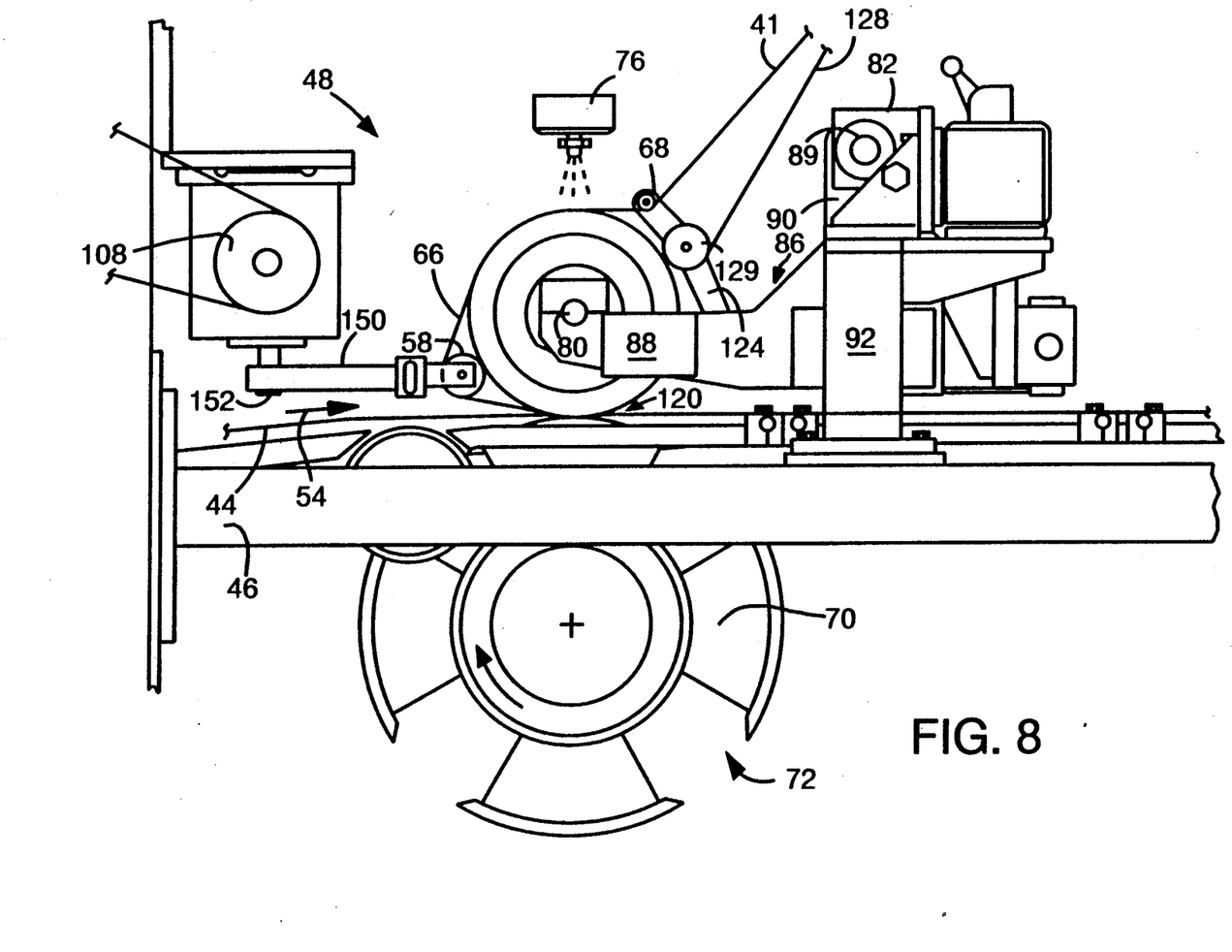
FIG. 8 representatively shows an alternative embodiment of the invention which includes a guiding means which oscillates about an optionally oriented axis of rotation.

In alternative configurations of the invention, such as representatively shown in FIG. 8, the guiding means can comprise a guide roller mounted on a pivotable arm 150 with the pivotable arm arranged to pivot about an axis 152 which is aligned generally perpendicular to substrate path 54. In addition, the axis may be aligned generally along elastic path 66 into the guiding means. For example, the longitudinal axis of pivot shaft 152 can be aligned generally perpendicular to substrate path 54. As a result, pivotable arm 150 can be configured to rotationally oscillate about the pivot shaft along a plane of oscillation which is generally parallel to substrate 44.

Figure 9:
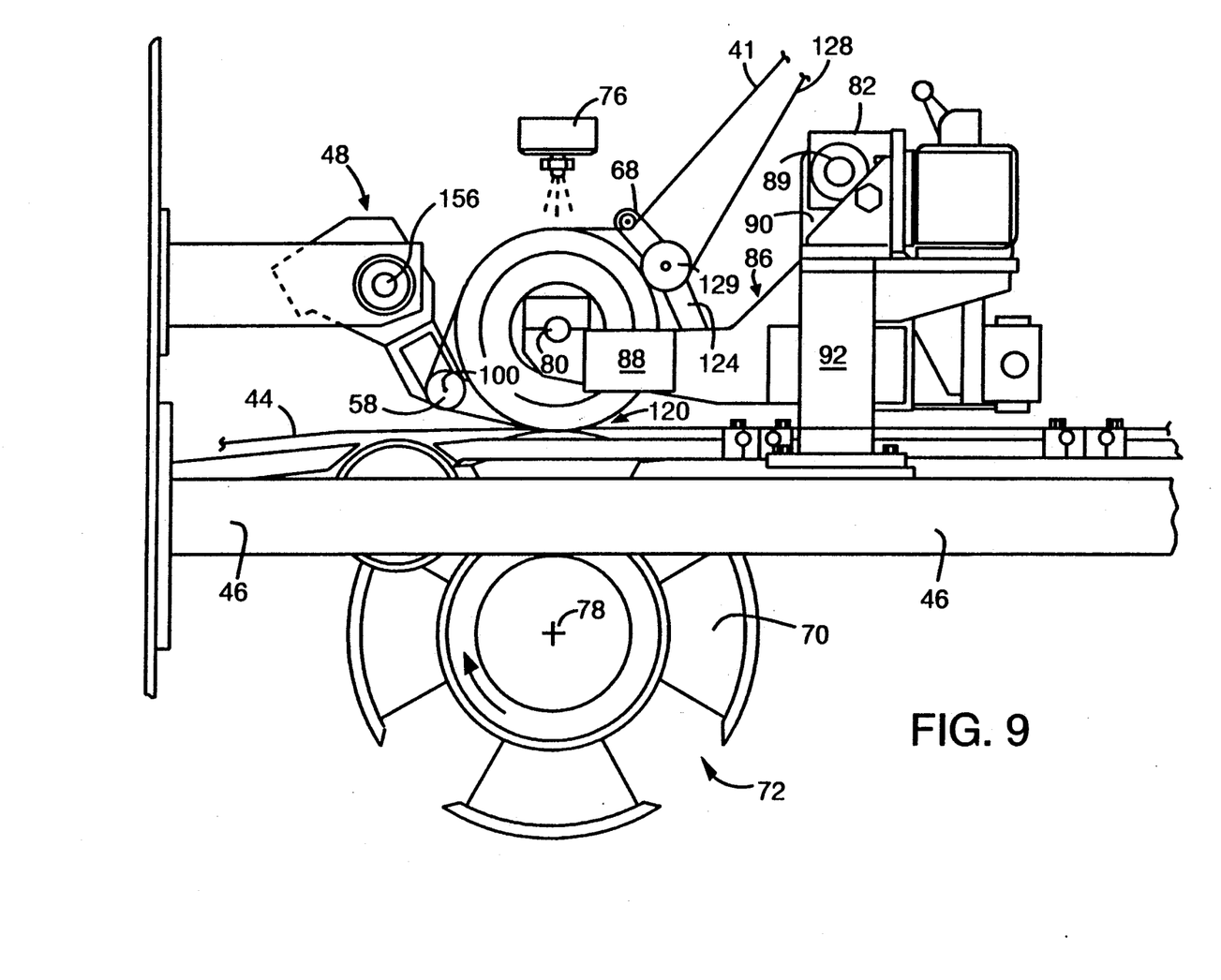
FIG. 9 representatively shows a side elevational view of an embodiment of the invention which includes a guiding means that linearly oscillates along a substantially straight-line path.
Figure 9A:
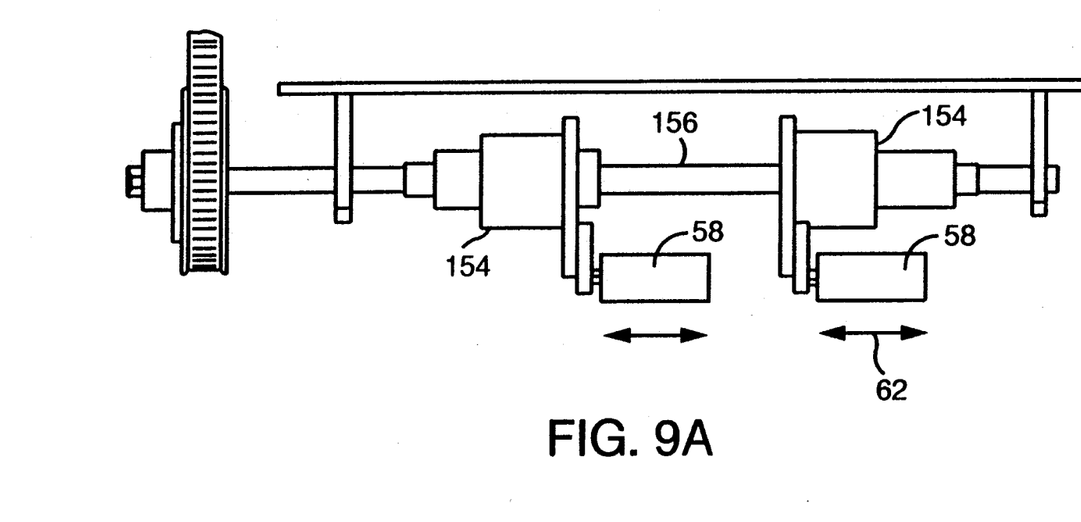
FIG. 9A representatively shows a top elevational view of the apparatus illustrated in FIG. 9.

In yet another alternative aspect of the invention, the guiding means can be configured with a guide roller 58 which oscillates along a substantially linear path directed along cross direction 62, as representatively shown in FIGS. 9 and 9A. For example, a suitable ball nut mechanism, ball screw mechanism or barrel cam mechanism 154 may be employed to linearly oscillate guide roller 58 along shaft 156. The rate and magnitude of the oscillation can be selectively regulated by conventional means.

Having thus described the invention in rather full detail, it is readily apparent that various changes and modifications can be made without departing from the spirit of the invention. All of such changes and modifications are contemplated as being within the scope of the present invention, as defined by the subjoined claims.

We claim:

1. An apparatus for applying an elastic member onto a substrate along a selected curvilinear location, said apparatus comprising:

transporting means for moving said substrate along a selected substrate path;

conveying surface for directing said elastic member along a selected elastic path;

elastic supplying means for providing said elastic member to said conveying surface;

a rotatable nip roll for placing said elastic member onto said substrate along said curvilinear location;

bonding means for providing an adhesive in an arrangement which secures said elastic member to said substrate along said curvilinear location;

means for providing a web to said conveying surface, said web arranged to carry said elastic member and to substantially prevent contact between said adhesive and said nip roll;

guiding means positioned along said elastic path for delivering said elastic member and said web from said conveying surface across a free-span distance onto said nip roll while selectively changing a lateral positioning of said elastic member relative to a predetermined cross-direction.

2. An apparatus as recited in claim 1, wherein said conveying surface comprises a portion of said nip roll.

3. An apparatus as recited in claim 1, wherein said conveying surface is constructed to deliver said elastic member along an elastic path which is oriented generally perpendicular to said substrate path.

4. An apparatus as recited in claim 1, wherein said guiding means includes a guide mounted on a pivotable arm, said arm arranged to pivot about an axis which is aligned generally along said substrate path and generally perpendicular to said elastic path into said guiding means.

5. An apparatus as recited in claim 1, wherein said guiding means includes a guide mounted on a pivotable arm, said arm arranged to pivot about an axis which is aligned generally perpendicular to said substrate path and generally along said elastic path into said guiding means.

6. An apparatus as recited in claim 5, wherein a cam mechanism is connected to said pivotable arm to pivot said arm through a selected arc in a selected movement pattern to change said lateral positioning of said elastic member in a selected periodic pattern.

7. An apparatus as recited in claim 1, wherein said elastic supplying means is constructed to provide a plurality of separate strands of elastomeric material, and said bonding means is constructed to secure said strands onto said web.

8. An apparatus as recited in claim 1, wherein said bonding means is located adjacent said conveying surface for depositing adhesive onto said elastic member for securing said elastic member to said substrate.

9. An apparatus as recited in claim 1, wherein said web arranged to substantially prevent contact between said adhesive and said guiding means.

10. An apparatus for applying an elastic member onto a substrate along a selected curvilinear location, said apparatus comprising:
    transporting means for moving said substrate along a selected substrate path;
    elastic supplying means for providing an elastomeric material:
    conveying surface for directing said elastomeric material along said selected elastic path;
    a rotatable nip roll for contacting said elastomeric material onto said substrate along said curvilinear location;
    means for providing a carrier web which supports said elastomeric material on said conveying surface to provide a composite elastic member;
    bonding means for providing an adhesive in an arrangement which secures said elastic member to said web and secures said elastic member to said substrate along said curvilinear location, said bonding means located adjacent said conveying surface;
    guiding means for delivering said composite elastic member from said conveying surface across a free-span distance onto said nip roll while selectively changing a lateral positioning of said composite elastic member relative to a predetermined cross-direction, said guiding means including a guide roller mounted on a pivotable arm, said arm arranged to pivot about an axis which is aligned generally along said substrate path and generally perpendicular to a selected elastic path into said guiding means.

11. An apparatus as recited in claim 10, further comprising a canting supplemental guide for conveying said composite elastic member along a line which is in a substantially parallel alignment with said pivot axis of said pivotable arm, and for imparting a twist to said elastic member prior to delivering said elastic member to said guiding means.

12. An apparatus as recited in claim 10, wherein said bonding means is located adjacent said conveying surface.

13. A method for applying an elastic member onto a moving substrate along a selected curvilinear location, said method comprising the steps of:
    moving said substrate along a selected substrate path;
    conveying an elastomeric material on a conveying surface along a selected elastic path;
    securing said elastomeric material onto a carrier web which supports said elastomeric material on said conveying surface to provide a composite elastic member;
    contacting said composite elastic member onto said substrate along said curvilinear location with a rotatable nip roll;
    securing said composite elastic member to said substrate along said curvilinear location;
    delivering said composite elastic member from said conveying surface across a free-span distance onto said nip roll while selectively changing a lateral positioning of said composite elastic member relative to a predetermined cross-direction, said delivering provided by moving said composite elastic member with a guide roller mounted on a pivotable arm pivoting about an axis which is aligned generally along said substrate path and generally perpendicular to a selected elastic path onto said guide roller.

14. A method as recited in claim 13, further comprising the step of depositing adhesive from a location adjacent said conveying surface onto said elastic member for securing said composite elastic member to said substrate.

15. A method as recited in claim 14, further comprising the steps of providing a plurality of individual, spaced-apart strands of said elastomeric material, and securing said strands to said carrier web.

16. A method as recited in claim 13, wherein said delivering step includes the steps of receiving said composite elastic member along a line which is in a substantially parallel alignment with said pivot axis of said pivotable arm; imparting a twist to said composite elastic member with a canting supplemental guide; and directing said composite elastic member to said guide roller.

17. A method as recited in claim 13, wherein said securing step includes the step of applying adhesive to said elastomeric material at a location adjacent to said conveying surface.

18. An apparatus as recited in claim 17, further comprising a canting supplemental guide for conveying said web and elastic strands along a line which is in a substantially parallel alignment with said pivot axis of said pivotable arm, and for imparting a twist to said web and elastic strands prior to delivering said web and elastic strands to said guiding means.

19. A method for applying an elastic member onto a substrate along a selected curvilinear location, comprising the steps of:

moving said substrate along a selected substrate path;

directing said elastic member along a selected elastic path with a conveying surface;

placing said elastic member onto said substrate along said curvilinear location with a rotatable nip roll;

providing an adhesive in an arrangement which secures said elastic member to said substrate along said curvilinear location;

providing a web to said conveying surface, said web arranged to support said elastic member on said conveying surface and to substantially avoid contact between said adhesive said conveying surface;

delivering said web and elastic member from said conveying surface along said elastic path; and guiding said web and elastic member from said elastic path across a free-span distance directly onto said nip roll while selectively changing a lateral positioning of said elastic member relative to a predetermined cross-direction.

20. A method as recited in claim 19, wherein said delivering step is arranged to deliver said elastic member from said conveying surface into said guiding step along an elastic path which is oriented generally perpendicular to said substrate path.

21. A method as recited in claim 19, wherein said guiding step includes the steps of moving said elastic member with a guide roller mounted on a pivotable arm, and pivoting said arm about an axis which is aligned generally along said substrate path and generally perpendicular to said elastic path into said guiding step.

22. A method as recited in claim 19, further comprising the steps of moving said elastic member with a guide roller mounted on a pivotable arm, pivoting said arm about an axis which is aligned generally perpendicular to said substrate path and generally along said elastic path into said guiding step.

23. An apparatus for applying an elastic member onto a substrate along a selected curvilinear location, said apparatus comprising:

transporting means for moving said substrate along a selected substrate path;

a rotatable nip roll for directing a plurality of elastic strands along a selected elastic path and for placing said elastic strands onto said substrate along said curvilinear location;

bonding means for providing an adhesive in an arrangement which secures said elastic strands to said substrate along said curvilinear location, said bonding means located adjacent a conveying surface of said nip roll;

means for providing a web to said conveying surface, said web arranged to carry said elastic and to substantially prevent contact between said adhesive and said nip roll;

guiding means positioned along said elastic path for delivering said elastic strands and said web from a conveying portion of said nip roll across a free-span distance onto a nip region said nip roll while periodically oscillating along a predetermined cross-direction through a selected angle to change a lateral positioning of said elastic member relative to said predetermined cross-direction, said web arranged to substantially prevent contact between said adhesive and said guiding means.

* * * * *